(12) United States Patent  
Greenwald et al.

(10) Patent No.: US 9,128,024 B2  
(45) Date of Patent: *Sep. 8, 2015

(54) TISSUE SPECIMEN HOLDER

(75) Inventors: Roger J. Greenwald, Holley, NY (US); James M. Zavislan, Pittsford, NY (US)

(73) Assignee: CALIBER IMAGING & DIAGNOSTICS, INC., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/020,387

(22) Filed: Dec. 22, 2004

(65) Prior Publication Data

US 2005/0157386 A1    Jul. 21, 2005

Related U.S. Application Data

(60) Continuation of application No. 09/973,109, filed on Oct. 9, 2001, now Pat. No. 6,856,458, which is a division of application No. 09/506,135, filed on Feb. 17, 2000, now Pat. No. 6,330,106.

(60) Provisional application No. 60/120,470, filed on Feb. 17, 1999.

(51) Int. Cl.
*G02B 21/34* (2006.01)
*G01N 21/03* (2006.01)
(Continued)

(52) U.S. Cl.
CPC ............ *G01N 21/0303* (2013.01); *B01L 3/508* (2013.01); *G02B 21/0028* (2013.01);
(Continued)

(58) Field of Classification Search
CPC ........... G02B 21/0032; G02B 21/0088; G02B 21/06–21/14; G02B 21/24; G02B 21/26; G02B 21/31–21/34
USPC ............... 359/665, 385–398, 798–801, 804; 436/176; 206/524.4, 456; 73/864.41–44, 864.51, 864.91; 435/305.1–305.4; 356/244, 246
See application file for complete search history.

(56) References Cited

U.S. PATENT DOCUMENTS

| 1,002,910 | A | 9/1911 | Foote ............................. 434/297 |
| 1,991,983 | A | 2/1935 | Newman ....................... 359/398 |

(Continued)

FOREIGN PATENT DOCUMENTS

| DE | 1472294 | 2/1969 | .................... 359/665 |
| DE | 22 10 442 A1 | 9/1973 | |

(Continued)

OTHER PUBLICATIONS

Gross, Kenneth G. et al., Mohs Surgery, Fundamentals and Techniques, 1999, p. 94.

(Continued)

*Primary Examiner* — Stephone B Allen
*Assistant Examiner* — James McGee
(74) *Attorney, Agent, or Firm* — Kenneth J. Lukacher Law Group (57) ABSTRACT

A tray or holder for tissue specimens, especially of excised tissue, such as biopsied specimens, is used with a confocal imaging system. The tray may be disposable after imaging of the specimen carried therein or may archive the specimen. A window supports the specimen. Clamps mounted inside the tray restrain the tissue. A compliant bag is mounted outside the tray on one side of a window of the tray on which the specimen is disposed. During imaging the specimen is immersed in a liquid contained in the tray having an index of refraction which closely matches the index of refraction of the tissue. The bag also contains an index matching liquid preferably having the same index as the liquid in the tray. Selecting an immersion liquid, which equals the refractive index of the near surface tissues, minimizes wavefront distortion which may result from an effectively corrugated surface of the specimen.

24 Claims, 6 Drawing Sheets

(51) Int. Cl.
*B01L 3/00* (2006.01)
*G02B 21/00* (2006.01)
*G01N 1/36* (2006.01)

(52) U.S. Cl.
CPC ............ *G02B21/34* (2013.01); *B01L 2300/043* (2013.01); *B01L 2300/0609* (2013.01); *B01L 2300/0654* (2013.01); *B01L 2300/0672* (2013.01); *B01L 2300/0822* (2013.01); *B01L 2400/0683* (2013.01); *G01N 1/36* (2013.01); *G01N 2021/0339* (2013.01); *G01N 2021/0342* (2013.01); *G01N 2021/0364* (2013.01)

(56) References Cited

U.S. PATENT DOCUMENTS

| | | | |
|---|---|---|---|
| 3,031,924 A | 5/1962 | Lamal | 359/398 |
| 3,202,049 A | 8/1965 | Bond | 359/665 |
| 3,510,194 A | 5/1970 | Connelly | 359/398 |
| 3,551,023 A | 12/1970 | Brackett | 156/60 |
| 3,556,633 A | 1/1971 | Mutschmann et al. | 359/398 |
| 3,648,587 A | 3/1972 | Stevens | 359/794 |
| 3,904,781 A | 9/1975 | Henry | 427/2.11 |
| 4,159,875 A | 7/1979 | Hauser | 356/244 |
| 4,208,101 A | 6/1980 | Trapp et al. | 359/656 |
| 4,257,346 A * | 3/1981 | Ornstein et al. | 118/641 |
| 4,545,831 A | 10/1985 | Ornstein | 156/57 |
| 4,744,643 A * | 5/1988 | Taylor | 359/398 |
| 4,752,347 A | 6/1988 | Rada | 156/382 |
| 4,965,441 A | 10/1990 | Picard | 250/201.3 |
| 4,974,952 A | 12/1990 | Focht | 359/398 |
| 5,034,613 A | 7/1991 | Denk et al. | 250/458.1 |
| 5,120,953 A | 6/1992 | Harris | 250/227.2 |
| 5,122,653 A | 6/1992 | Ohki | 250/216 |
| RE34,214 E | 4/1993 | Carlsson et al. | 348/79 |
| 5,257,128 A * | 10/1993 | Diller et al. | 359/395 |
| 5,296,963 A | 3/1994 | Murakami et al. | 359/389 |
| 5,311,358 A | 5/1994 | Pederson et al. | 359/510 |
| 5,367,401 A | 11/1994 | Saulietis | 359/398 |
| 5,383,472 A | 1/1995 | Devlin et al. | 128/771 |
| 5,503,741 A | 4/1996 | Clark | 210/232 |
| 5,532,874 A | 7/1996 | Stein | 359/394 |
| 5,675,700 A | 10/1997 | Atwood et al. | 392/382 |
| 5,681,741 A | 10/1997 | Atwood et al. | |
| 5,719,700 A | 2/1998 | Corcuff et al. | 359/368 |
| 5,788,639 A | 8/1998 | Zavislan et al. | 600/476 |
| 5,812,312 A | 9/1998 | Lorincz | 359/397 |
| 5,836,877 A | 11/1998 | Zavislan | 600/407 |
| 5,843,674 A | 12/1998 | Takimoto et al. | 435/7.1 |
| 5,870,223 A | 2/1999 | Tomimatsu | 359/392 |
| 5,880,880 A | 3/1999 | Anderson et al. | 359/385 |
| 5,995,283 A | 11/1999 | Anderson et al. | 359/385 |
| 6,048,723 A | 4/2000 | Banes | 435/305.1 |
| 6,272,235 B1 | 8/2001 | Bacus et al. | 382/133 |
| 6,330,106 B1 | 12/2001 | Greenwald et al. | 359/398 |
| 6,411,434 B1 | 6/2002 | Eastman et al. | 359/398 |
| 6,493,460 B1 | 12/2002 | MacAulay et al. | 382/133 |
| 6,856,458 B2 * | 2/2005 | Greenwald et al. | 359/398 |

FOREIGN PATENT DOCUMENTS

| | | |
|---|---|---|
| DE | 32 20 702 A1 | 12/1983 |
| JP | 56 113115 | 9/1981 |
| WO | WO 96/21938 | 7/1996 |

OTHER PUBLICATIONS

Schmitt, Joseph M et al., Optical Characterization of Dense Tissues Using Low-coherence Interferometry, 1993, SPIE vol. 1889, pp. 197-211.
Rajadhyaksha, M. et al., Confocal Laser Microscope Images Tissue In Vivo, Laser Focus World, Feb. 1997, pp. 119-127.
Rajadhyaksha, M. et al., In Vivo Confocal Scanning Laser Microscopy of Human Skin: Melanin Provides Strong Contrast, The Journal of Investigative Dermatology, Jun. 1995, vol. 104, No. 6, pp. 946-952.
Brochure, Looking Through the Window of Life, Lucid VivaScope, The Confocal Scanning Laser Microscope, Lucid Technologies, Inc.
Smith, W., Modern Optical Engineering, The Design of Optical Systems, McGraw-Hill, Inc. Second Edition, Chapter 4, pp. 96-99, 1990.
Nuovo, G. et al., An Improved Technique for the In Situ Detection of DNA After Polymerase Chain Reaction Amplification, American Journal of Pathology, vol. 139, No. 6, pp. 1239-1244, (1991).

* cited by examiner

TISSUE SPECIMEN HOLDER

This application is a continuation of U.S. patent application Ser. No. 09/973,109, filed Oct. 9, 2001, now U.S. Pat. No. 6,856,458, which is a divisional of U.S. patent application Ser. No. 09/506,135, filed Feb. 17, 2000, now U.S. Pat. No. 6,330,106, which claims the priority benefit of U.S. Provisional Application No. 60/120,470, filed Feb. 17, 1999, which is herein incorporated by reference.

The present invention relates to a tissue specimen holder or tray for use in microscopy and particularly in laser scanning confocal microscopy for imaging sections of surgically excised specimens. The invention is especially suitable for providing a tissue tray which aids in the imaging of a wide variety of tissue samples which may be excised tissues or biopsies of various tissues, such as liver, kidney, cervix, et cetera.

It has been proposed to provide for the imaging of specimens in an immersion liquid which matches the index of refraction of the tissue (See U.S. Pat. No. 5,719,700, issued Feb. 17, 1998 to P. Corcuff, et al and U.S. Pat. No. 4,208,101, issued Jun. 17, 1980 to L. Trapp, et al). Handling of the tissue specimens and the immersion liquid is difficult. The specimens are small and the liquid can run over a slide on which the specimen is mounted. In short, handling and preparation of specimens for imaging is, with the proposed systems, a messy operation. In addition, variations in optical path between the section of the specimen of interest and the imaging system can distort the image. Such distortions are exacerbated by the corrugated surface provided at the surface of the specimen. For high fidelity imaging, the immersion fluid must closely match the tissue index. Matching the refractive index of the immersion fluid to the tissue greatly reduces the optical refracting power of tissue and therefore the optical path difference introduced by the tissue.

It is a feature of the invention to provide specimen holders or tissue trays optimized for different tissues which are usable with the same imaging system, and without replacement or adjustment of objective lenses. The tray provided by the invention may be used to contain the specimen for short term or long term storage or to transport the tissue for additional processing. The tray may be disposable after use. The tray contains and also has associated therewith index matching liquids. The tray facilitates the use of such liquids without messy operations and without adversely affecting imaging (imparting distortion to the image because of the presence of the index matching liquids).

The confocal laser scanning microscope imaging systems having objective lenses which are capable of forming images of different sections having different orientations within a specimen may be of the type described in allowed U.S. patent application Ser. No. 08/683,607 filed Jul. 15, 1996 in the name of R. Rox Anderson et al., now U.S. Pat. No. 5,880,880, issued Mar. 9, 1999, and U.S. Pat. No. 5,788,639, filed in the names of James Zavislan and Jay Eastman and issued Aug. 4, 1998.

Briefly described, a specimen holder in accordance with the invention includes a container having a window through which an optical beam passes into a specimen disposed in the container over the window. The container may be in the form of a specimen tray. The specimen is preferably held in place by clamps which may be automatically applied when a cover of the container is closed. In use, the container includes an immersion liquid which closely matches the index of the tissue. Matching may be to the average index at the surface of the tissue which interfaces with the window. The tissue surface may be corrugated due to natural or surgically produced surface texture. Such corrugation may alter the wavefront of the beam (make the wavefront depart from a section of a sphere) which enters the tissue and is focused in the tissue section of interest. The distortion due to such variations is reduced in accordance with the invention by virtue of minimizing the variation of optical path lengths, notwithstanding that the section at which the beam is focused may be at the surface of the tissue or within the tissue (for example a distance of up to approximately 3 mm from the surface) by use of immersion liquids and coupling liquids and other transmissive elements, including the window, through which the imaging beam passes. The coupling medium is contained in a bag outside the container and facing the window. The bag is made of compliant transmissive material such as a polymer, for example polyethylene, but is of a minimum thickness so as not to have any material effect on the optical path through the bag. The bag contains a liquid coupling medium. Mounted on the bag is a stabilizing plate of transmissive material. The plate is opposed to the window, and preferably contains a lock-in unit such as a magnet or magnetic ring which is received in a notch at the top of a barrel containing the objective lens of the imaging system. The objective lens and the tray is supported on a fixture which is mounted on a common structure with the objective lens via a translation mechanism, which moves the fixture and the container in nominally orthogonal directions, one of which is along the optical axis of the lens. The index of the coupling medium is preferably the same as the index of the immersion liquid. The tray may have a passageway which is pierced by a protrusion on the cover of the tray so as to allow the coupling liquid to fill the tray and provide the immersion liquid. The stabilizing coupling of the plate to the objective lens prevents tilting and maintains the plate perpendicular to the optical axis notwithstanding of motion of the container so as to bring sections of the specimen of interest into focus and to scan the specimen in the plane of the section. In order to minimize optical distortion, due to changes in optical path between the exit pupil of the objective lens and the section of the specimen being imaged, in spite of the corrugations caused by the surface, the difference between the index of refraction of the immersion liquid and the average index of refraction of the tissue at it's surface, multiplied by the height between the peaks of the hills and bottoms of the valleys of the corrugations, is selected to be equal or less than a quarter wavelength at the wavelength of the laser beam used for imaging. Since the average index is a function of tissue type and clinical condition of the patient, the index matching fluids can be selected in the preparation of the tray for the particular tissue to be imaged. In addition, the thickness and index of the window and the plate may be varied depending upon the type of tissue in the tray in order to reduce spherical aberration for the objective lens used in the imaging system.

The foregoing and other features, objects and advantages of the invention will become more apparent from a reading of the following description taken in connection with the accompanying drawings in which:

FIG. 1 is a diagram schematically showing the imaging system, its objective lens and a container providing a tray with the tray in one of two alternative positions, where the section is near the surface of the tissue sample, while FIG. 1B shows the position where the section is within the tissue sample (specimen);

FIG. 1A is an enlarged view of the section shown within the dashed lines labeled 1A-1A in FIG. 1;

Referring more particularly to FIGS. 1, 1A, 1B, 2 and 7, there is shown a tissue holder or tray 10 mounted on a support platform 12. The support platform 12 is moveable by a translation mechanism 14 which is mounted on a stand 16 which holds an objective lens assembly 18 in a nominally fixed position. The platform 12, translation mechanism 14 and stand 16 provide a tray support fixture which can receive various trays. The lens assembly 18 includes a lens barrel 20 and a lens 22 mounted within the barrel. The upper end of the barrel has an annular notch 24 in which a portion of the tray 10 is received and locked, as will be discussed in greater detail below.

The tissue tray or holder 10 is an assembly having a generally open specimen container or box with a plate providing a base 26, sidewalls 28 and a cover 30, which may be hinged to one of the side walls. The shape of the box is shown as rectangular but it may be circular or oblong. The base has an opening containing a window 32 of transparent material. The thickness and refractive index of this window is selected to accommodate the design of the lens 18 and the index of refraction of the tissue specimen 34. The specimen may be surgically excised.

Figure 3:
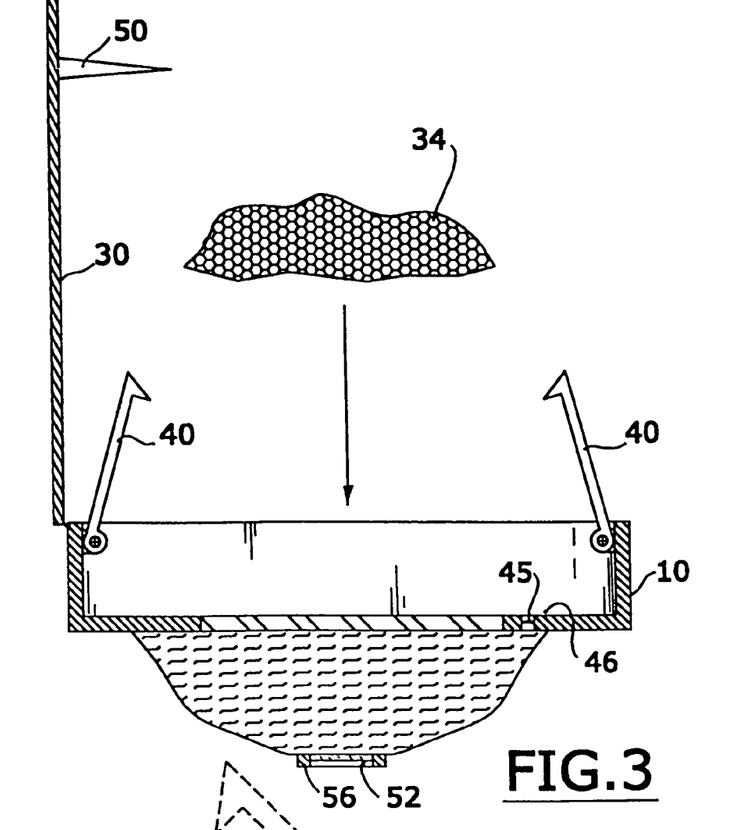
FIG. 3 is a diagram showing the tray in process of preparation.

A compliant bag 44 of thin, optically transparent material, is attached to the underside of the base 26 of the tray 10. This bag is initially filled with an optical coupling medium which may also provides an immersion medium for the specimen 34. To prepare the tray, the specimen 34 is placed on the window 32 as shown in FIG. 3. Clamping mechanisms 40 are then used to hold down the tissue specimen on the window for viewing, as shown in FIG. 5. The mechanisms are shown engaging the specimen 34 in FIG. 5, but may automatically engage the specimen when the cover is closed, as shown in connection with FIG. 4. When the cover is closed, a pin 50, carried on the cover, pierces a plug 45 in an opening 46 which provides a passageway for the flow of the coupling medium into the tray through the pierced opening 46. When the tray 10 is placed on the support platform, a transparent stabilizing plate 52 which is attached to the bag 44 in a location near the bottom of the bag opposite to the window 32, is captured in the notch 24 at the upper end of the lens barrel. The relative heights of the platform 12 and the lens barrel 24, both of which are supported in the fixture 16, is such that the bag 44 is compressed by the lens barrel and the shape thereof changes from the shape shown in FIG. 5 to the shape shown in FIG. 6. Then the liquid optical coupling medium 39 flows through the hole 46 and encompasses the specimen. The coupling liquid then serves as the immersion liquid. In another embodiment of the invention, the tray may be filled with the immersion liquid, and, when the plug is pierced, the immersion liquid flows into the bag. In a further embodiment, the bag and tray are independently filled. When plug 45 is opened the fluids can mix. In a further embodiment the bag and tray are independently filled. There is no plug 45 and the liquids remain separate.

In either case, the height of the liquid above the lens and above the base depends upon the relative position of the tray and may vary as the tray is moved to select the focus in the section of the specimen to be imaged. See FIG. 1B. The configuration of the bag also changes as the tray moves with respect to the objective lens 18 to scan the section.

The objective lens 18 may be a generic lens which is corrected for spherical aberrations for a cover slip of certain index $N_T$ and thickness T. The spherical aberration present in the objective lens is equal and opposite the spherical aberration introduced by the cover media or slip. When the focus is adjusted to the top surface of window 32, the cover medium includes plate 52, coupling medium 39, and window 32. The spherical aberration can be described by several representations such as longitudinal ray aberration, transverse ray aberrations or wavefront aberration. Using the longitudinal ray aberration, the spherical aberration=$LA_T$. The longitudinal aberration can be minimized by a single plate of index $N_T$ and thickness T or a series of plates such that where the plate is in air, $$LA_T(N_T, T) = \sum_{i=1}^{i=N} LA_T(N_i, t_i),$$

$$\text{where, } LA(N_i, t_i) = \frac{t_i}{Ni}\left[1 - \frac{N_i \cos U}{\sqrt{N_i^2 - \sin^2 U}}\right]$$

and where U is the angle in air with respect to the optical axis of the marginal ray in the converging beam. $N_i$ and $t_i$ is the index and thickness of each of the plates. The relationships when the plate is liquid are similar. See Warren Smith, Optical Engineering, pages 96-99 published by McGraw Hill, (1990) for further information on the equations given above.

Figure 8:
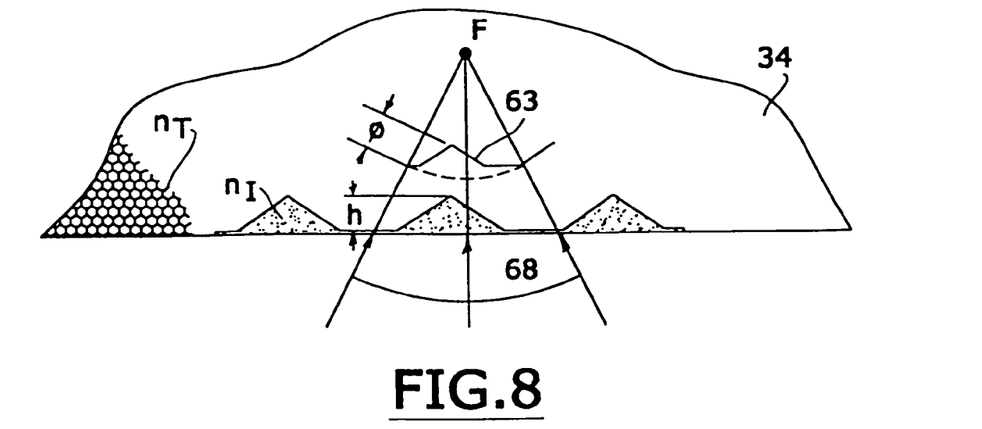
FIG. 8 is an enlarged view schematically illustrating the corrugations formed by surface texture at the surface of the tray.

Aberration is introduced by the specimen and particularly by the surface texture of the specimen in the optical path (along the axis of the lens 18). A laser beam from a confocal imaging system 36 passes through the lens along the optical path and is focused in the specimen. The tissue defines a corrugated surface as shown in FIG. 8. There is index variation between the tissue surface and the window 32, which may be accommodated in part, by a selection of the index and thickness in the direction of the beam (along the optical axis) through the window 32. The other indices of refraction of the elements in the beam path are also taken into account in determining the thickness and index of either the window 32, plate 52, or both. The primary determinative of the index and thickness of the window 32 is the index of the tissue of the specimen 34. Thus, the index and thickness of the window 32 (or plate 52) will depend upon the type of specimen being imaged. Different trays 10 are provided for different types of specimens (kidney, liver, cervix, et cetera) and each will have a somewhat different window thickness and index in order to reduce spherical aberration.

An immersion liquid 38 having an index which generally matches the average index of the tissue of the specimen 34 is contained in the tray. This liquid may serve also as a tissue preservative or fixative.

Figure 4:
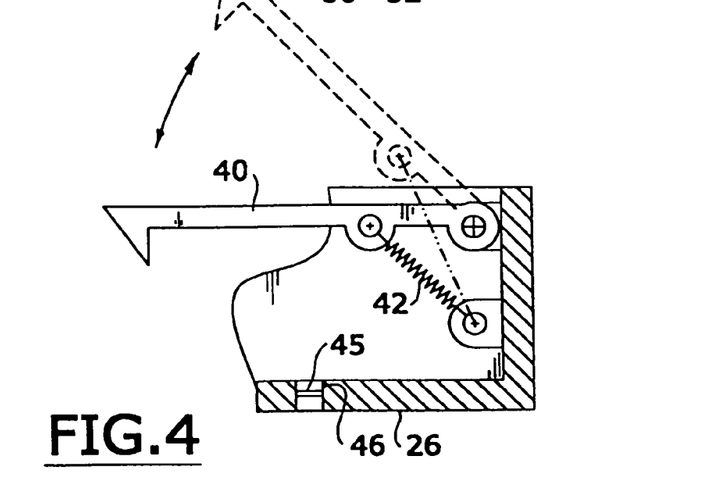
FIG. 4 is an enlarged view illustrating one of the clamp mechanisms used in the tray.
Figure 4A:
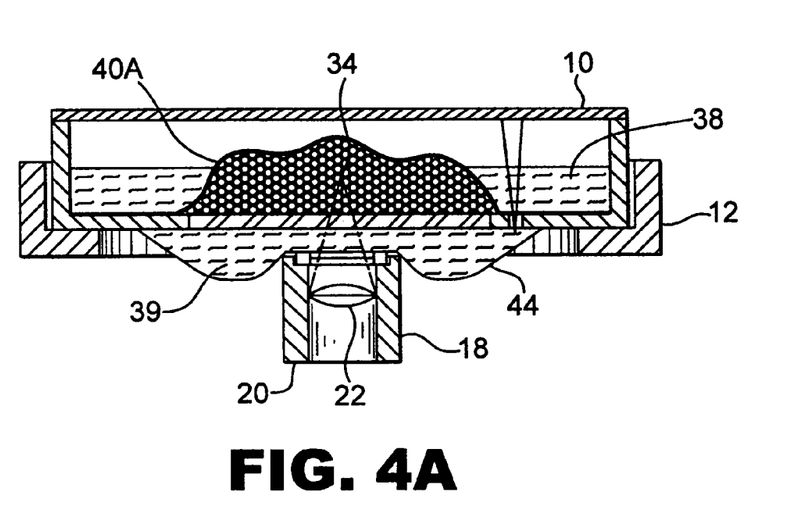
FIG. 4A is a diagram similar to FIG. 1B showing another clamping mechanism.
Figure 5:
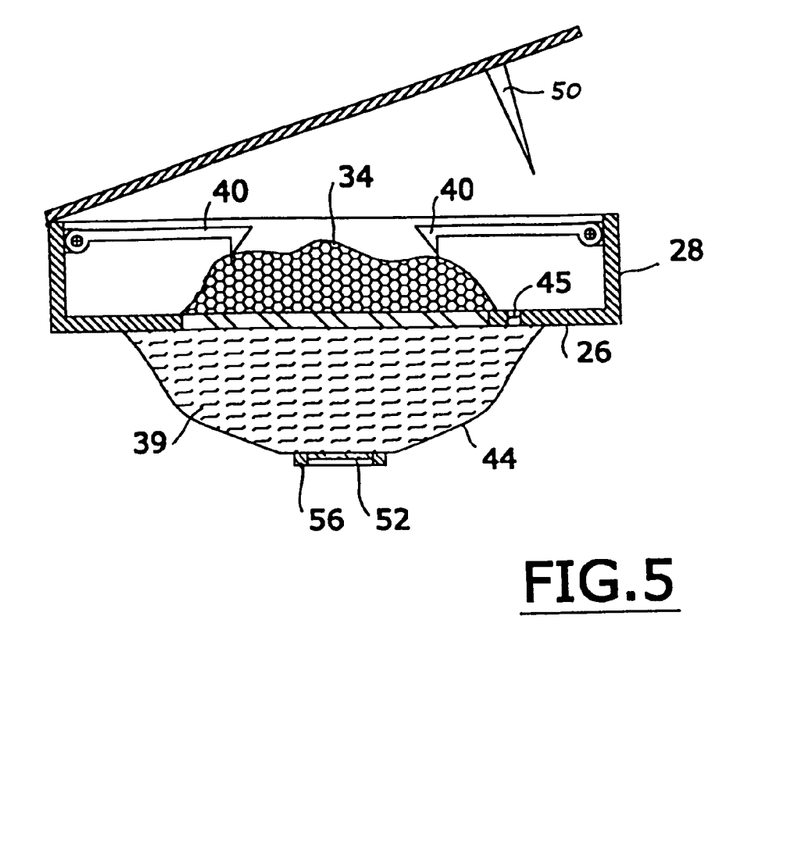
FIG. 5 is a diagram illustrating the tray where the cover is in process of being closed.

When the tissue specimen 34 is placed in the tray in the base 26 and over the window 32 as shown in FIGS. 3 and 4, the specimen 34 is held down by the clamp mechanism 40. The clamp mechanism which is illustrated has hooked or barbed fingers which are hinged to the sidewalls 28 at spaced locations. The mechanisms include springs 42 which provide over center locks, such that when the fingers are pressed down beyond their axis of rotation, they are held down by the springs 42. Other clamping mechanisms may be used such as meshes or a membrane overlay 40A or a permeable or perforated bag (FIG. 4A). Fiducial marks, which can be visualized or imaged, may be provided in the case of meshes or membranes. The use of a membrane or mesh may be preferable since the specimen 34 may be moved under the membrane. The membrane specimen tray or cassette is the subject matter of a companion application in the name of Eastman, et al., U.S. patent application Ser. No. 09/502,252, filed Feb. 17, 2000, now U.S. Pat. No. 6,411,434, having priority to U.S. Provisional Application No. 60/120,534, filed Feb. 17, 1999. Further information as to the use of the markings on the clamping mechanism (the mesh or membrane) to mark locations of the image tissue is contained in a co-pending International Patent Application No. PCT/US99/21116, and U.S. patent application Ser. No. 09/786,902, filed Mar. 9, 2001, now U.S. Pat. No. 6,745,067, filed in the names of Roger J. Greenwald and James M. Zavislan, having priority to U.S. Provisional Application No. 60/100,176 through International Patent Application No. PCT/US99/21116. The purpose of the clamps is to keep the tissue stationary during examination and also provide a means to lightly compress the tissue surface against the window. Alternatively, the clamps may provide tension to pull the tissue surface taut. Holding the tissue with either compression normal to the window or in tension parallel to the window (or both) tends to reduce the surface texture, or corrugation, peak to valley depth.

Figures 1, 1A:
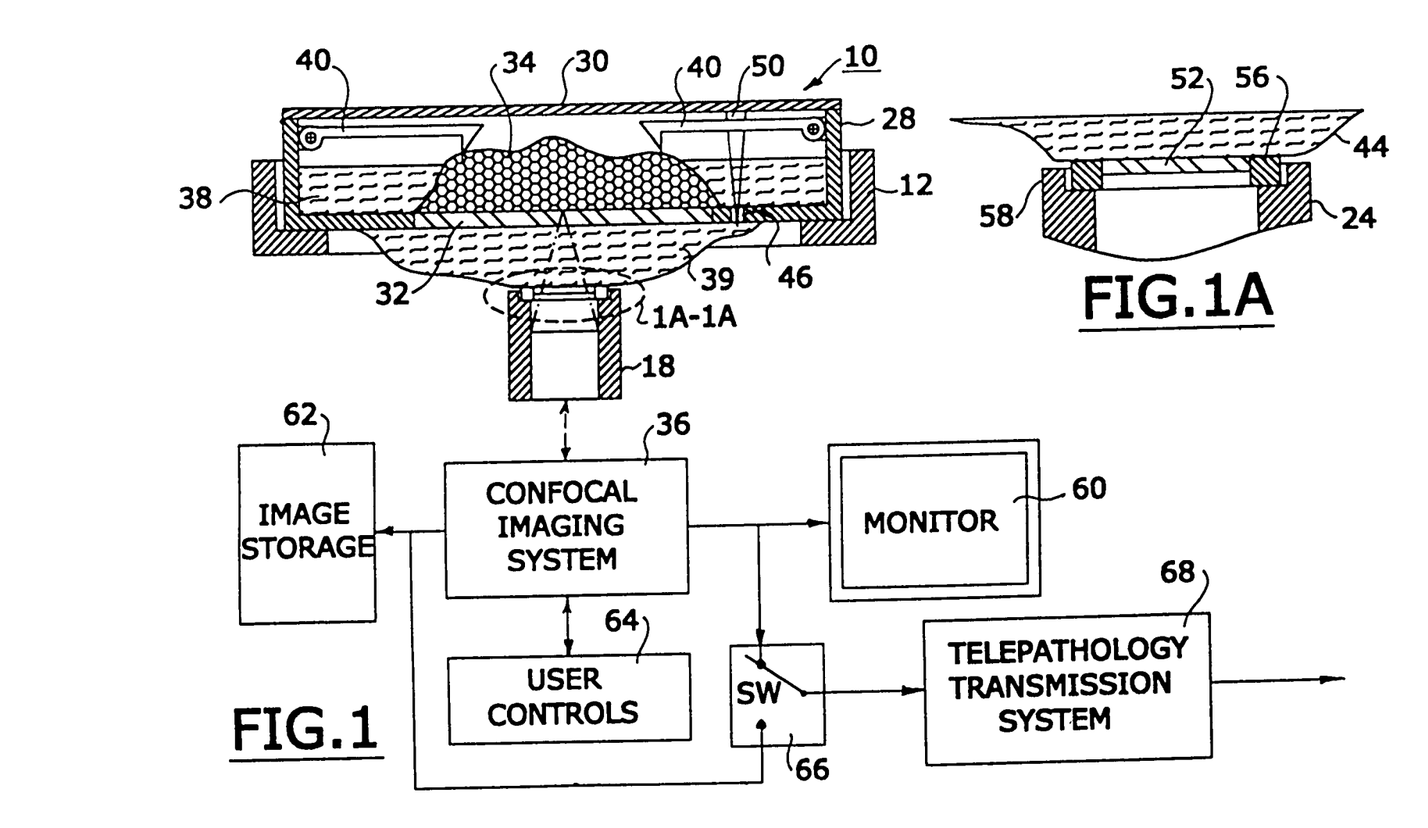
Figure 6:
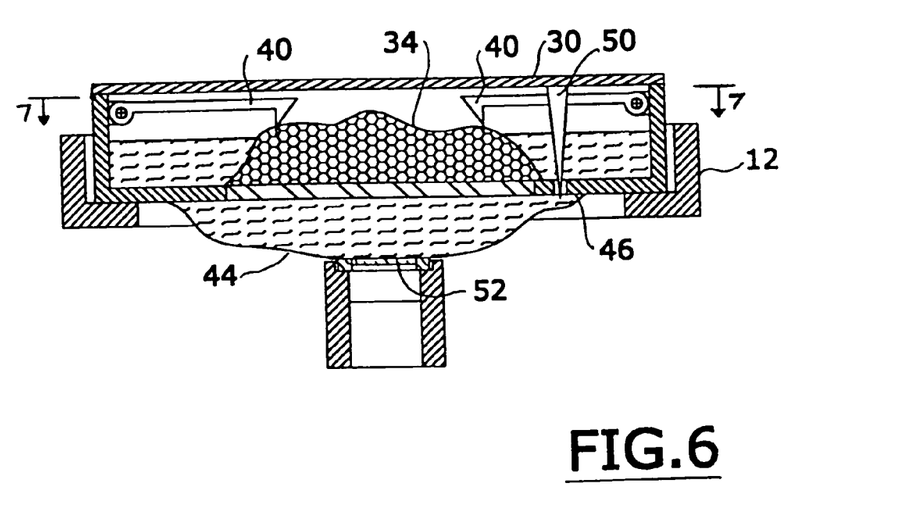
FIG. 6 is a view similar to FIG. 5 showing the tray after closure of the tray.
Figure 7:
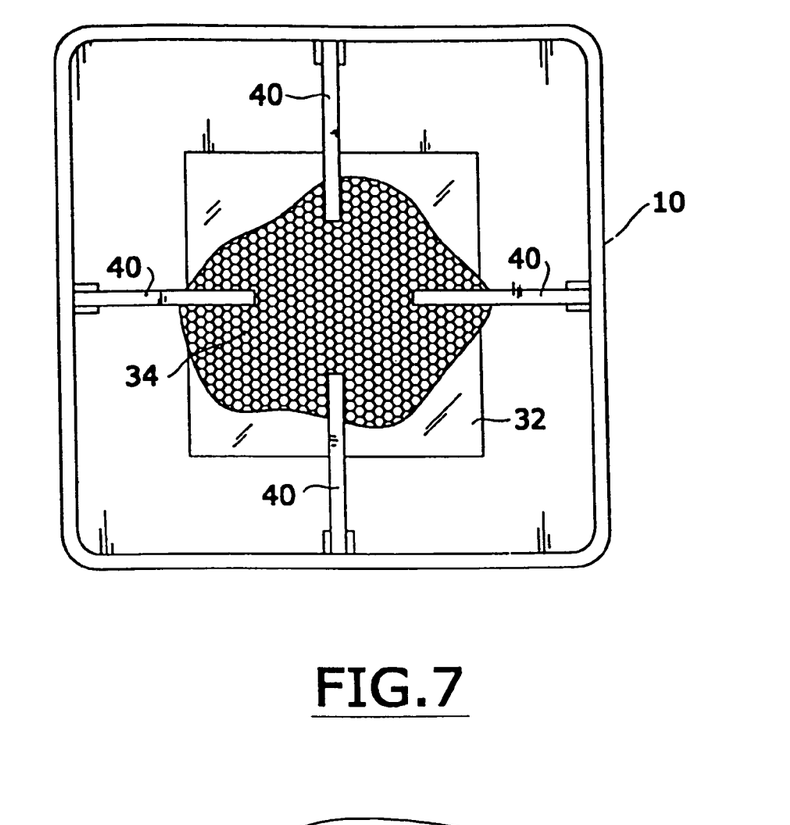
FIG. 7 is a sectional top view taken along the line 7-7 in FIG. 6.

As shown in FIG. 1, the thin compliant bag 44 is attached to the base 26 and encompasses the window 32 and the initially plugged opening 46. The bag is filled with the optical coupling medium 39, which may have an index selected in order to reduce image distortion due to the corrugations formed by the texture surface of the specimen 34 via which the optical imaging beam passes. Preferably the coupling liquid is the same as the immersion liquid 38 and the coupling liquid may flow through the opening 46 which may initially have a plug 45 and be plugged and then opened by the pin 50 carried by the cover 30, when the cover is closed as shown in FIG. 6.

The stabilizing plate 52 is attached to the bag 44 opposite to the window 32. This plate has an index of refraction and thickness which is taken into account in selecting the thickness and index of the window 32. A magnet or magnetic ring 56 surrounds the plate 52. See FIG. 1A. The plate 52 may be held by fusing, welding, cementing, friction or screw fit into the ring 56. The ring is permanently attached, as by a fused or cemented connection, to the bag 44, or to an opening in the bag. The diameter of the ring 52 is sized to fit into a notch 58 at the upper end of the barrel of the objective lens. The barrel may be made of magnetic material so as to lock the bag 44 in place on the assembly of the objective lens 18. The attachment is removable since the hold down force is magnetic. Other removable or releasable lock in mechanisms, such as snaps, may be used. The plate 52 may be curved or of a meniscus shape to provide optical power added to the power of the objective, if desired.

The confocal imaging system 36 may be of the type described in the above referenced Anderson and Zavislan patents. Imaging systems using two-photon microscopy or optical coherence tomography may also be used. See Denk et al., U.S. Pat. No. 5,034,613 and Schmitt et al., Proc. SPIE, volume 1889 (1993). Associated with the imaging system is a monitor or display 60 which provides a display of the image of the section. The image may also be stored digitally in memory shown as image storage 62. The location of the section being imaged is obtained by user controls 64 which may provide signals for actuating drive motors or other actuators in the translation mechanism 14 which selects the section to be imaged and can scan the section. Alternatively, the translator stage may be manually controlled by the use of micrometers. The image storage 62 or the imaging system may be connected through a switch 66 to a telepathology transmission system 68 which transmits the image to a remote location. Such a system 68 is the subject of U.S. Pat. No. 5,836,877 issued Nov. 17, 1988 to J. Zavislan.

Figure 1B:
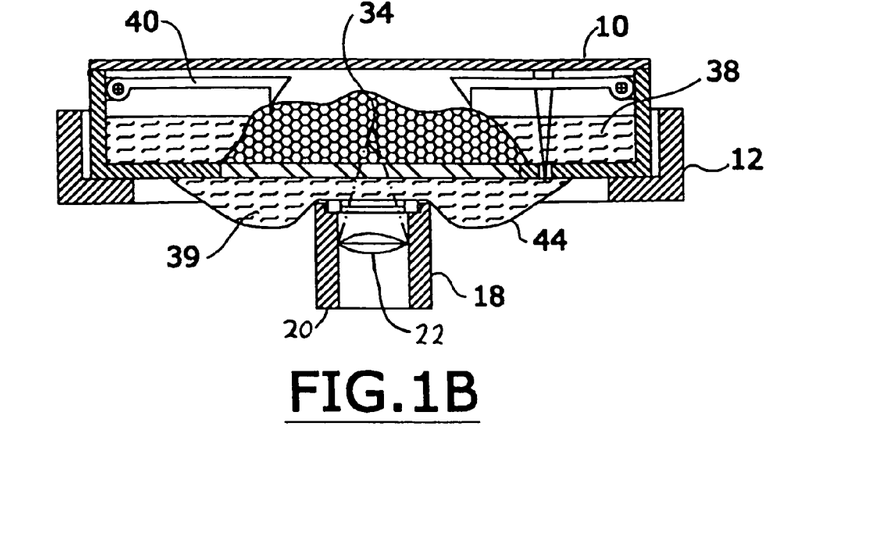
FIG. 1B shows the objective lens and tray where the beam is focused at an image plane within the specimen, where the section being imaged is located.
Figure 2:
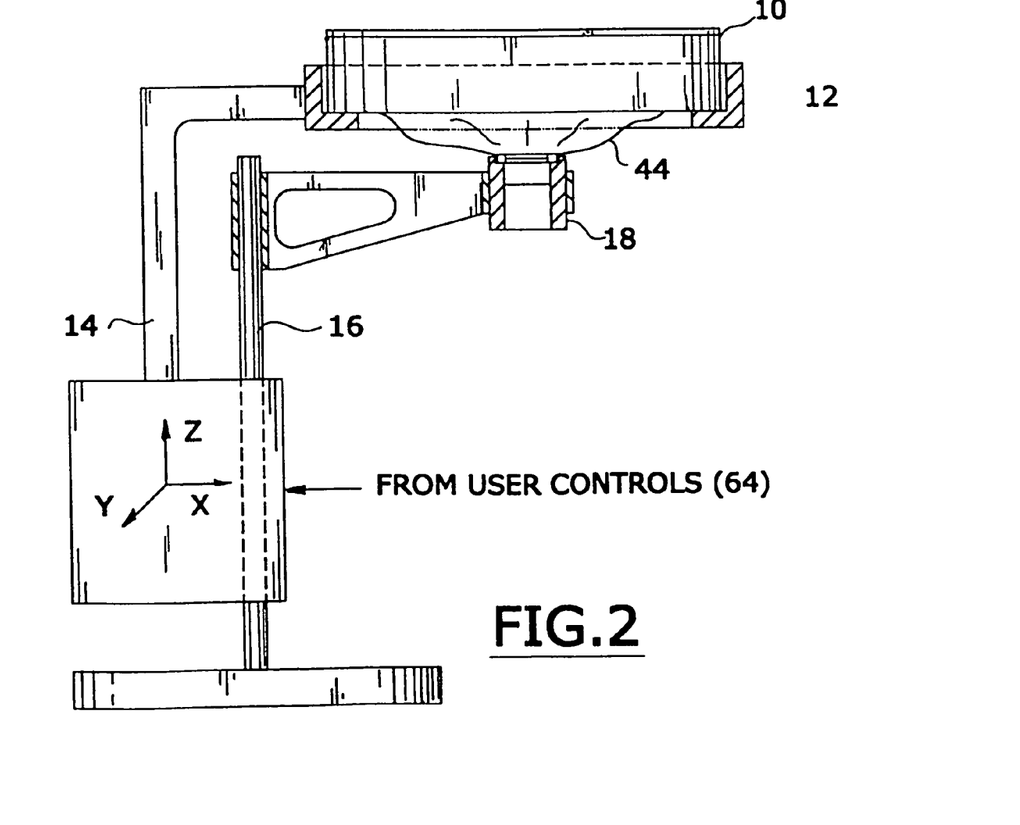
FIG. 2 is a diagram illustrating the fixturing for the tray and the mechanism for adjusting the position of the tray in three orthogonal directions, X, Y, and Z.

As shown in FIGS. 1 and 1B, the lens 18 may focus the beam at the surface or within the specimen by moving the support 12 thereby varying the distance between the lens and the tray. As the distance along the optical axis to that inside the tissue changes, the thickness along that axis of the coupling and medium 39 varies in an opposite sense. This keeps the optical path constant, even though the section may be well within the specimen. This inverse relationship of bag thickness to focus depth is in a direction to compensate for aberration due to physical length variations between the lens and the section of the medium being imaged.

As shown in FIG. 8, the corrugations due to the surface texture of the specimen 34 creates corrugations having a depth (h) (from the apex of the corrugation peaks to the bottom of the valleys of the corrugations) which may be approximately 200 microns in length. The index of refraction of the tissue is $n_T$, while the index of refraction of the immersion fluid, which fills the corrugations providing the surface texture of the specimen 34, have an index $n_I$. The beam is focused at a focus f in the section to be imaged. The wavefront which may be spherical, can be distorted due to an optical path difference $\phi$ imprinted on the wavefront which converges to the focus F. This path difference is a function of the product of the corrugation height h and the difference between $n_T$ and $n_I$. The use of the index matching fluid reduces the optical path difference so that the imprint is minimized. The optical path difference $\phi$ is shown enlarged at 63 in FIG. 8. This optical path difference may also be viewed as the wavefront which is propagating to the focus F. This wavefront may be spherical and part of a sphere as shown at 68 prior to passing through corrugations at the surface of the specimen 34. The optical path distortion after transmission through the tissue surface is approximated by the relation $$\phi = h(n_T - n_I)$$

where h is the mechanical depth of surface texture. In order to correct for the distortion of the beam wavefront (which may be a spherical wavefront) by virtue of the variation in index of refraction presented by corrugations, it is desirable that the difference in index of the immersion liquid 38 and the average index of refraction of the tissue multiplied by the corrugation height h that is the optical path distance between the hills and valleys of the corrugation), not exceed a quarter wavelength of the laser beam which is used for imaging in the imaging system 36. Thus, the immersion medium is selected for the tissue type which is placed in the tray and substantially corrects for optical distortion due to the surface texture of the specimen.

In operation, the tray and the specimen are prepared by placing the tissue therein, and positioning the tissue. The tray is then placed in the support 12 and the magnet lock in 56 connects the tray to the objective lens. The lid is closed, piercing the membrane or plug covering opening 46, allowing coupling media to flow upwardly from the bag 44 attached to the bottom portion of tray 10. In an alternative embodiment, the tray may be filled with the immersion liquid before closing the lid and flows down into bag 44 upon lid closing. Then, under operation of the user controls 64, the beam is focused at the section and scanned across the section so as to obtain images of that section. A bar code, or other indicia, may be applied to the tray 10, as on its cover or a side wall for identification and tracking of the specimen, which is especially useful when the tray and specimen are archived (stored for later examination or other use).

Variations and modifications in the herein described apparatus and its method of operation, within the scope of the invention, will undoubtedly suggest themselves to those skilled in the art. Accordingly, the foregoing description should be taken as illustrative and not in a limiting sense.

The invention claimed is:

1. A device for supporting excised tissue during imaging of said excised tissue having a refractive index comprising:
   a window having a surface for imaging through upon which excised tissue is locatable;
   at least one member for restraining said excised tissue against said window to keep at least one surface of the excised tissue against said window when said excised tissue is located upon said surface of said window; and
   a liquid medium disposed with the excised tissue when located upon said surface of said window, said liquid medium having an index of refraction selected in accordance with the index of refraction of said at least one surface of said excised tissue so that said immersion medium minimizes differences in optical path length of an illumination beam when transmitted through said at least one surface of the excised tissue and extending below said at least one surface of the excised tissue to at least one location in the excised tissue.

2. The device according to claim 1 wherein said illumination beam has a wavefront, said at least one surface of the excised tissue has texture which distorts the wavefront of the illumination beam, said liquid medium substantially fills corrugations formed by said texture, and said refractive index of said liquid medium is selected in accordance with at least a refractive index of the excised tissue and to minimize the distortion of said illumination beam due to said texture.

3. An apparatus for imaging excised tissue having a refractive index comprising:
   a container for excised tissue having a window upon which said excised tissue is disposed;
   at least one member for restraining said excised tissue which keeps at least one surface of the excised tissue against said window;
   a liquid immersion medium in said container having an index of refraction;
   an illumination beam; and
   optics directed towards the window and the excised tissue for imaging one or more sections below said at least one surface of the excised tissue through the window with said illumination beam, wherein said index of refraction of said immersion medium is selected in accordance with the index of refraction of said at least one surface of said excised tissue so that said immersion medium minimizes differences in optical path length of the illumination beam when transmitted through said at least one surface of the excised tissue and extending below said at least one surface of the excised tissue to at least one location in the excised tissue where said one or more sections are being imaged.

4. The apparatus according to claim 3 wherein said illumination beam has a wavefront, said at least one surface has texture which distorts the wavefront of the illumination beam, said liquid immersion medium substantially fills corrugations formed by said texture, and said refractive index of said liquid immersion medium is selected in accordance with at least the refractive index of the excised tissue and to minimize the distortion of the wavefront of the illumination beam due to said texture.

5. An apparatus for imaging excised tissue having a refractive index comprising:
   a container for excised tissue having a window with a surface;
   at least one member for restraining said excised tissue upon said surface which keeps at least one surface of the excised tissue against said window;
   a liquid immersion medium in said container having an index of refraction;
   an illumination beam; and
   optics directed towards the window and the excised tissue for imaging one or more sections below said at least one surface of the excised tissue through the window with said illumination beam, wherein said refractive index of said immersion medium is selected in accordance with the index of refraction of said at least one surface of said excised tissue so that said immersion medium minimizes differences in optical path length of the illumination beam transmitted through said at least one surface of the excised tissue to the one or more sections when imaged below said at least one surface of the excised tissue.

6. The apparatus according to claim 5 wherein said container is a tray.

7. The apparatus according to claim 5 wherein said container is one of a plurality of containers of different types each for a different type of said excised tissue, said window has a thickness, and said thickness of said window and said refractive index of said liquid immersion medium are both varied among different ones of said plurality of containers for reducing spherical aberration in said illumination beam in accordance with the type of excised tissue when in the container.

8. The apparatus according to claim 5 wherein said member maintains said excised tissue stationary and against said window.

9. The apparatus according to claim 5 wherein said member comprises a finger for applying pressure down upon said excised tissue.

10. The apparatus according to claim 5 wherein said member comprises a mesh for applying pressure down upon said excised tissue.

11. The apparatus according to claim 5 wherein said member comprises a membrane for applying pressure down upon said excised tissue.

12. The apparatus according to claim 5 wherein said optics for imaging optically forms an image of each of said one or more sections of the tissue specimen in which the optically formed image is usable for pathology.

13. The apparatus according to claim 5 wherein said optics are part of an imaging system operable by one of confocal microscopy, two-photon microscopy or optical coherence tomography.

14. The apparatus according to claim 5 wherein said optics provide an optical path for said illumination beam which is invariant through said excised tissue.

15. The apparatus according to claim 5 wherein said illumination beam has a wavefront, said at least one surface has texture which distorts the wavefront of the illumination beam, said liquid immersion medium substantially fills corrugations formed by said texture, and said refractive index of said liquid immersion medium is selected in accordance with at least the refractive index of the excised tissue and to minimize the distortion of the wavefront of the illumination beam due to said texture.

16. The apparatus according to claim 15 wherein said corrugations have depth, and said member reduces the depth of said corrugations of said at least one surface of the excised tissue against said surface of said window.

17. The apparatus according to claim 15 wherein said illumination beam has a wavelength, and a non-zero difference between the index of refraction of the liquid immersion medium and an average of the index of refraction of said excised tissue near said at least one surface of said excised tissue, multiplied by a height between peaks of hills and bottoms of valleys of said corrugations along said at least one surface of said excised tissue that is illuminated by said illumination beam, is equal or less than a quarter wavelength at the wavelength of said illumination beam.

18. The apparatus according to claim 5 further comprising means disposed between said container and said optics which presents another medium between said container and said optics optically coupling said optics to said container.

19. The apparatus according to claim 18 wherein said another medium presented between said container and said optics has a refractive index equal to the refractive index of said liquid immersion medium in said container.

20. The apparatus according to claim 5 wherein said another medium presented between said container and said optics is separate from the liquid immersion medium in said container.

21. A method for imaging excised tissue having a refractive index and at least one surface comprising the steps of:
providing a container having a window;
restraining excised tissue in said container against said window to keep at least one surface of said excised tissue against said window;
imaging one or more sections of said excised tissue through said window using an illumination beam; and
providing a liquid immersion medium in said container having an index of refraction selected in accordance with the index of refraction of said at least one surface of said excised tissue so that said immersion medium minimizes differences in optical path length of the illumination beam when transmitted through at least one surface of the excised tissue and extending below said at least one surface of the excised tissue to at least one location in the excised tissue where said imaging of one or more sections is being carried out.

22. The method according to claim 21 wherein said container provided is one of a plurality of containers of different types each for a different type of said excised tissue, said window has a thickness, and said thickness of said window and said refractive index of said liquid immersion medium are both varied among different ones of said plurality of containers for reducing spherical aberration in said illumination beam in accordance with the type of excised tissue when in the container.

23. The method according to claim 21 wherein said restraining step is carried out with aid of at least one member for restraining said excised tissue which keeps said at least one surface of the excised tissue against said window.

24. The method according to claim 21 wherein said at least one surface of said excised tissue has texture, and said providing step provides said liquid immersion medium which substantially fills corrugations formed by the texture of said at least one surface of said excised tissue and minimizes wavefront distortion of said illumination beam due to said texture.

* * * * *